US005598266A

United States Patent [19]
Cornuejols

[11] Patent Number: 5,598,266
[45] Date of Patent: Jan. 28, 1997

[54] DEVICE FOR DETECTING DEFECTS REMOVED FROM FIBROUS MATERIAL USING OPTICAL INSPECTION

[75] Inventor: Georges Cornuejols, Montpellier, France

[73] Assignee: Le Centre De Cooperation Internationale En Recherche Agronomique Pour Le Developpement (CIRAD), Paris, France

[21] Appl. No.: 367,229

[22] PCT Filed: Jul. 22, 1993

[86] PCT No.: PCT/FR93/00753

§ 371 Date: Jan. 18, 1995

§ 102(e) Date: Jan. 18, 1995

[87] PCT Pub. No.: WO94/02838

PCT Pub. Date: Feb. 3, 1994

[30] Foreign Application Priority Data

Jul. 22, 1992 [FR] France .................................. 92 09258

[51] Int. Cl.⁶ .............................. G01J 4/00; G01N 21/00; G01N 21/84
[52] U.S. Cl. ...................... 356/367; 356/369; 356/370; 356/238; 356/239; 356/430; 250/559.09; 250/559.11; 250/559.41; 250/559.46
[58] Field of Search ..................... 356/237–239, 356/424–431, 364, 366–367, 369–370, 38; 250/559.08, 559.09, 559.11, 559.41, 559.45–559.47

[56] References Cited

U.S. PATENT DOCUMENTS

| | | | |
|---|---|---|---|
| 3,451,756 | 6/1969 | Young | 250/559.12 |
| 4,402,604 | 9/1983 | Nash | 356/237 |
| 4,632,596 | 12/1986 | Sick et al. | 356/237 |
| 4,648,053 | 3/1987 | Fridge | 356/390 |
| 4,976,540 | 12/1990 | Kitamura et al. | 356/38 |
| 5,130,559 | 7/1992 | Leifeld et al. | 250/562 |
| 5,295,401 | 3/1994 | Toedtli | 356/429 |
| 5,383,135 | 1/1995 | Shofner et al. | 364/552 |
| 5,430,301 | 7/1995 | Shofner et al. | 356/238 |

FOREIGN PATENT DOCUMENTS

| 1411254 | 10/1975 | United Kingdom . |
|---|---|---|
| 2095828 | 10/1982 | United Kingdom . |

OTHER PUBLICATIONS

Database WPIL Week 8840, Derwent Publications Ltd., London, GB; AN 88-284004 & SU-A-1 382 887 (ALMA) 23 Mar. 1988.

*Primary Examiner*—Frank Gonzalez
*Assistant Examiner*—Jason D. Eisenberg
*Attorney, Agent, or Firm*—Oblon, Spivak, McClelland, Maier & Neustadt, P.C.

[57] ABSTRACT

A device for detecting defects (2, 3) in fibrous materials (4, 22) includes members (16, 17) for squeezing the material against a film (1), a separating member (24) downstream of the squeezing members for separating the fibrous material from the film, and an opto-electronic sensor (6) downstream of the separating member for imaging the film and defects. An image processing assembly (26, 44) is electrically connected to the output of the imaging assembly for sensing and counting the marks left on the film by the defects. A member (25) is provided for moving the film relative to the optoelectronic sensor. Various optical systems, particularly polarizers (9, 10), may be incorporated into the device.

10 Claims, 3 Drawing Sheets

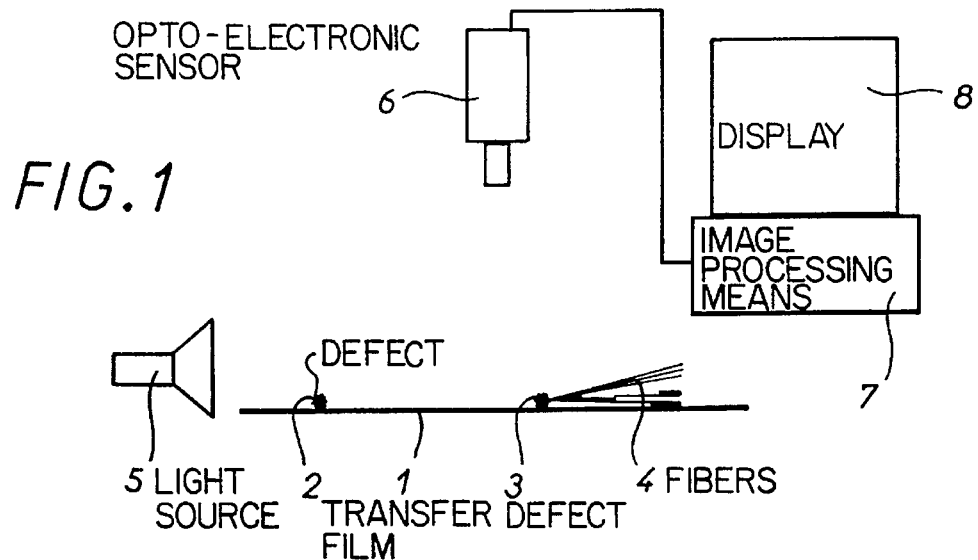
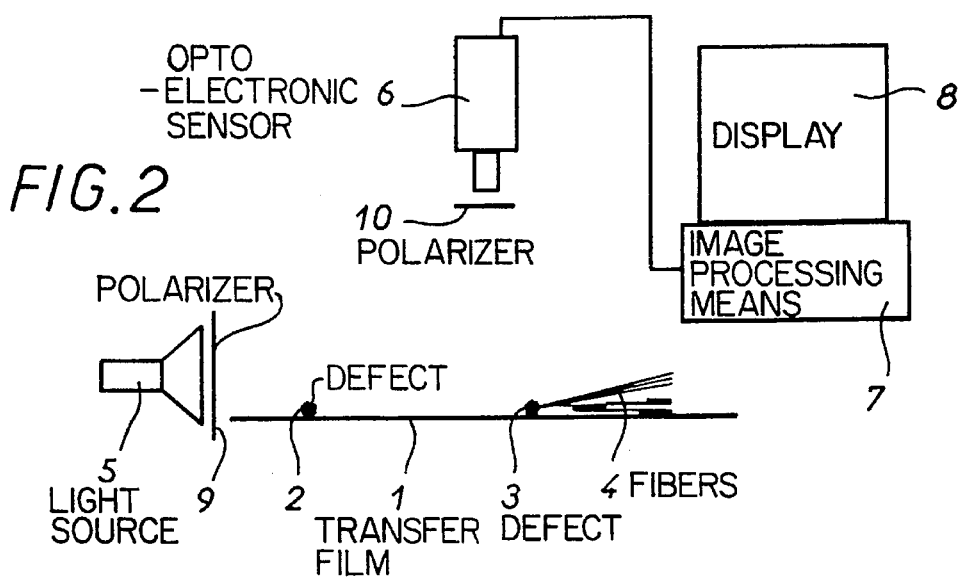
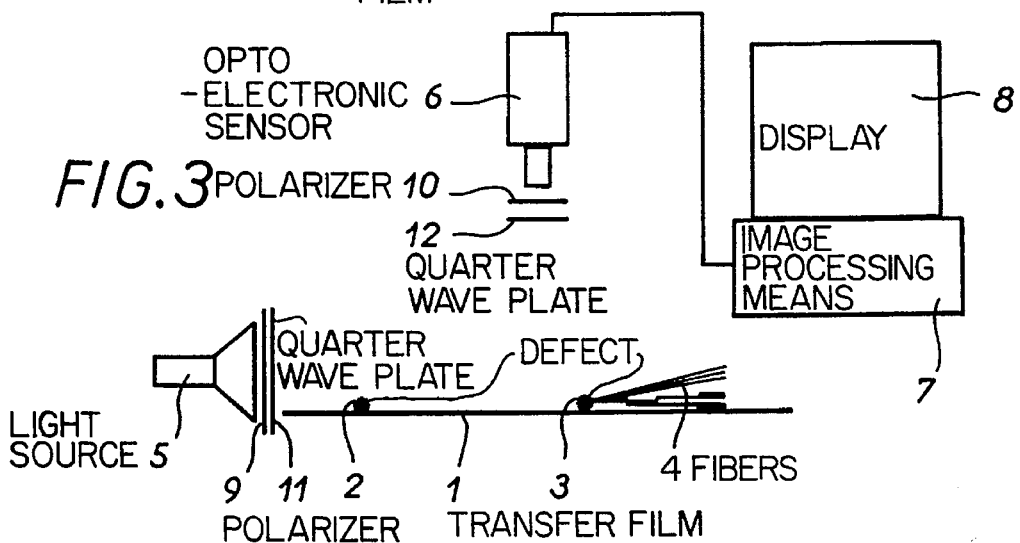

DEVICE FOR DETECTING DEFECTS REMOVED FROM FIBROUS MATERIAL USING OPTICAL INSPECTION

BACKGROUND OF THE INVENTION

1. Field of he Invention

The present invention concerns a device for detecting and for automatically counting defects in fibrous materials.

2. Discussion of the Background

The present invention applies in particular to measuring the amount of sticky sugars in cotton.

Fibrous materials, usually of plant origin, such as paper, cotton and wood are subject to homogeneity defects, inclusion of materials of different maturity and inclusions of materials foreign to the process of obtaining the materials concerned: insects, seeds, sugars, sticky sugars, artificial detritus.

Various devices have been developed for detecting such defects but are neither automatic nor fast in operation.

Where cotton is concerned, the devices known at this time, of the type which heat and cool a carding web disposed between two aluminum sheets, are limited to ocular counting, i.e. counting by the human eye, of spots of sticky sugars on an aluminum sheet.

SUMMARY OF THE INVENTION

The present invention intends to remedy this drawback by proposing a fully automatic device which is able to measure various types of defects in fibrous materials, even very fine defects. To detect the defects and the fibers of the material on an artificial support the invention uses combined polarizers on the light source and on an opto-electronic sensor.

The device of the present invention is a device for detecting defects in fibrous materials consisting of elements with an optical singularity, for example sugar particles in cotton, including an opto-electronic sensor adapted to produce signals representative of defects present in an optical field of the sensor, which is connected to image processing means adapted to analyze the signals representative of defects and to count them, characterized in that it includes a transfer film moved in the field of the opto-electronic sensor by feed means and passing in succession under means for pressing the fibrous material onto the transfer film so as to cause to adhere to the latter either defects with no fibers adhering to them or defects with fibers adhering to them, and under means for separating the fibrous material from the film so that the latter enters the field of the sensor carrying only the defects.

BRIEF DESCRIPTION OF THE DRAWINGS

The following description given by way of non-limiting explanatory example with reference to the appended drawings provides a better understanding of the advantages, objects and features of the invention.

FIG. 1 shows a first embodiment of an optical part of the device of the invention;

FIG. 2 shows a second embodiment of an optical part of the device of the invention;

FIG. 3 shows a third embodiment of an optical part of the device of the invention;

DESCRIPTION OF THE PREFERRED EMBODIMENTS

Figure 4:
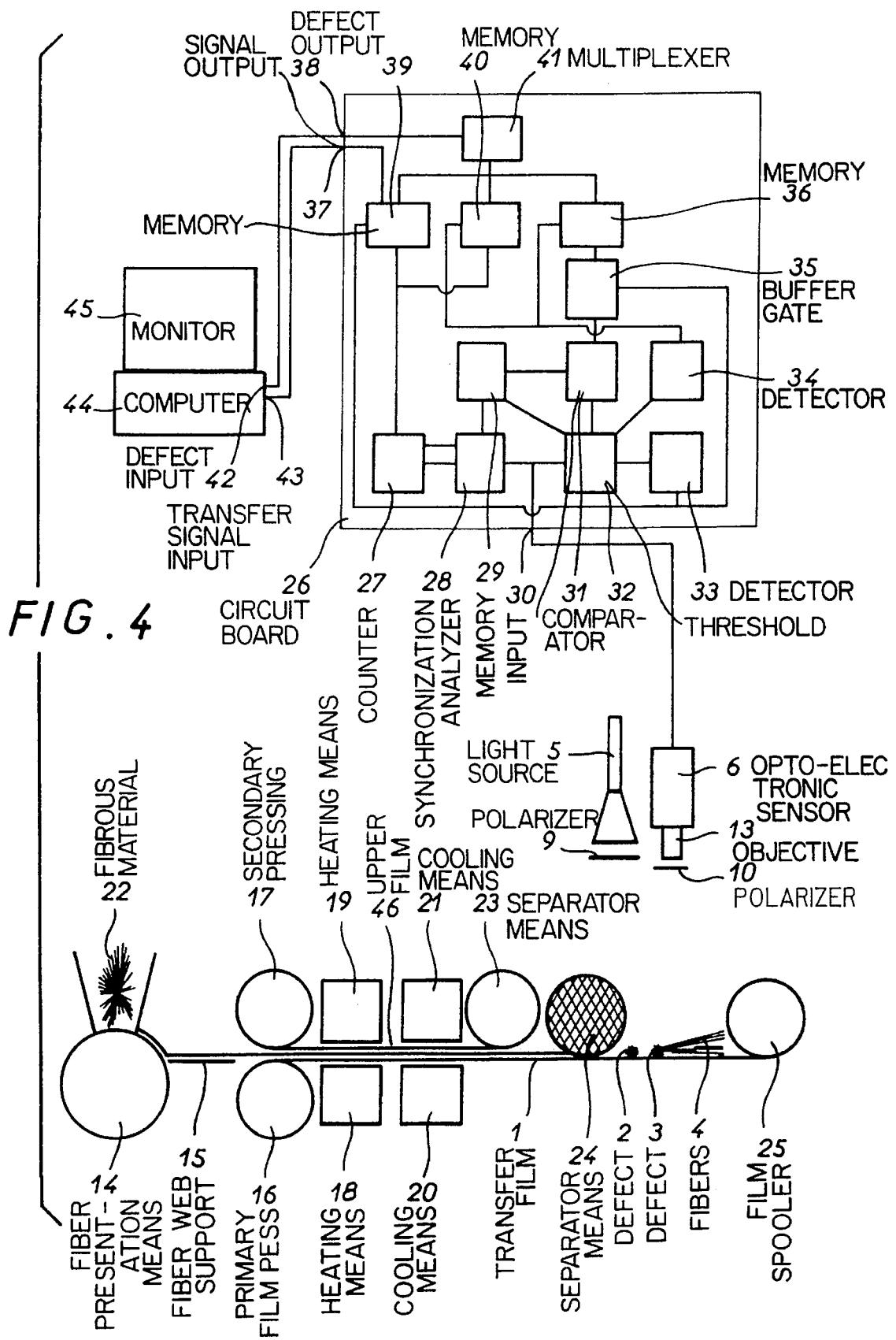
FIG. 4 shows a preferred embodiment of the device of the present invention.

FIG. 1 shows a transfer film 1 onto which have been transferred elements with an optical singularity constituting defects in fibrous materials; the defects 2 have not entrained any fibers with them but the defects 3 (sticky defects) have entrained with them fibers 4 extracted from the fibrous material. The device also includes a light source 5, an opto-electronic sensor 6, image processing means 7 and a display 8.

The transfer film 1 can be of metal, plastics material or an optically absorbent material depending on the type of optical singularity characteristic of the defects looked for and the nature of the fibers in which defects are to be detected. If the defects are sticky sugars in cotton, for example, the transfer film 1 can be of aluminum. If the defects in the cotton are sugar, the film 1 can be of paper or an absorbent material. A third option is for the film 1 to be coloured, i.e. to absorb some light rays for at least one wavelength sensed by the opto-electronic sensor 6. Finally, the material of film 1 can be a combination of the above materials.

The defects 2 without fibers are attached to the film 1 but are not attached to fibers of the material inspected. The defects 3 are attached to the film 1 and to at least one fiber of the material inspected.

The defects 2 and 3 are in the form of stains or deposits on the film 1. They locally modify the optical appearance of the film 1 as observed by the opto-electronic sensor 6. For example, the defects 2 and 3 partially absorb some wavelengths or depolarize the light or have a diffusion or reflection cone different than that of the film 1.

The light source 5 is adapted to illuminate the defects 2 and 3 and the fibers 4. For example, the light source 5 is a bulb energized continuously or intermittently, in the latter case synchronized to the formation of images by the opto-electronic sensor 6, or a laser source scanning the optical field of the opto-electronic sensor 6.

The opto-electronic sensor 6 is adapted to output an electrical signal representative of the image it perceives. It is adapted to perceive an image of the film 1, of the defects 2 and 3 and of the fibers 4.

The opto-electronic sensor 6 is a linear or matrix video camera or a photo diode, for example.

The image processing means 7 are adapted to process the electrical signal representative of images output by the opto-electronic sensor 6, in order to extract therefrom information concerning the defects 2 and 3 in the optical field of the opto-electronic sensor 6. The image processing means can be electronic circuits, computers with appropriate software or neural networks, for example. The image processing means 7 can include output connectors for information resulting from processing of the images or a printer.

The display 8 is adapted to display the results of the image processing carried out by the image processing means 7. This display can be a computer monitor, a video monitor or a flat screen, for example.

FIG. 2 includes all the same components as FIG. 1, plus a polarizer 9 associated with the light source 5 and a polarizer 10 associated with the opto-electronic sensor 6.

The polarizers 9 and 10 are linear polarizers, which means that for at least one wavelength sensed by the opto-electronic sensor 6 they absorb light rays polarized in a given plane of polarization. The polarizers 9 and 10 are crossed, i.e. the polarizer 10 is adapted to absorb light rays reaching it directly from the polarizer 9.

The optical part shown in FIG. 2 is designed for depolarizing defects 2 and 3 and fibers 4. Accordingly the film 1 is made from a non-depolarizing material so that the light polarized by the polarizer 9 and reaching the sensor 6, either directly or reflected from the film 1 in the field of the sensor where there are no defects, is blocked by the polarizer 10 and the field appears dark. The light partially depolarized by the defects 2 and by the defects 3 with their adhering fibers will reach the sensor 6 and will appear light against the dark background.

In a first variant of the embodiment of the invention shown in FIG. 2 at least one of the polarizers 9 and 10 is dichroic, i.e. has two orthogonal polarization axes polarizing light rays at different wavelengths. In this embodiment of the invention the opto-electronic sensor 6 is a color sensor, i.e. the electrical signal representative of images that it outputs also represents the wavelength of the light rays that the opto-electronic sensor perceives.

In a second variant of the embodiment of the invention shown in FIG. 2 the polarizer 10 has two areas with orthogonal polarization axes and the opto-electronic sensor 6 has two areas adapted to receive light rays from respective areas of the polarizer. An arrangement of this kind can be obtained, for example, by using a camera including two sensors separated by a prism, the two faces of the prism facing the two sensors being associated with polarizers with mutually orthogonal polarization axes.

In both these variants, the opto-electronic sensor is adapted to output a signal representative of at least two images, one of these images representing the optical appearance of the film with one polarization of light and another of these images representing the optical appearance of the film with a second polarization.

FIG. 3 shows the same components as FIG. 2 plus two quarter-wave plates 11 and 12 respectively disposed between the polarizers 9 and 10 and the film 1. The combination of a linear polarizer and a quarter-wave plate constitutes a circular polarizer.

The above description of FIG. 2 therefore applies also to FIG. 3, subject to substitution for the remarks therein on linear polarization of remarks on circular polarization.

Note that both quarter-wave plates operate with the same direction of rotation and that reflection at the film 1 reverses the direction of rotation of circularly polarized light rays. As a result, the images picked up by the opto-electronic sensor 6 are light for the defects 2 and 3 or for the fibers, respectively, and dark for the film 1.

FIG. 4 shows a complete device for inspecting cotton for sticky sugar defects on aluminum sheets.

FIG. 4 shows the film 1 carrying the defects 2 with no fibers and the defects 3 with fibers 4 adhering to them, a light source 5 carrying a first polarizer 9, an opto-electronic sensor 6 having an objective 13 carrying a second polarizer 10, a computer 44 having a defect information input 42 and a transfer signal input 43, a monitor 45, continuous fiber presentation means 14, a fiber web support 15, primary film pressing and dispenser means 16, secondary pressing and dispenser means 17 for an upper film 46, lower heating means 18, upper heating means 19, lower cooling means 20, upper cooling means 21, a sample of fibrous material 22, separator means 23 for the upper film 46, separator means 24 for the material, a lower film spooler 25, an image processing electronic circuit board 26 carrying a counter 27, a synchronization analyzer 28, a memory 29, an electronic circuit board input 30, a comparator 31, a threshold comparator 32, a rising edge detector 33, a falling edge detector 34, a buffer gate 35, three memories 36, 39 and 40, a multiplexer 41, a transfer signal output 37 and a defect information output 38.

This figure is described in detail in the chronological order of transfer of a sample of fibrous material 22 and of information concerning the material.

The fibers constituting the sample of fibrous material 22 and the film 1 move from left to right as seen in FIG. 4, a motor (not shown) rotating the spooler 25.

The image processing electronic circuit board 26 and the computer 44 together constitute the image processing means shown in FIGS. 1 to 3 and 5.

The sample of fibrous material 22 is formed by the continuous fiber presentation means 14 into a web known as a carding web in the cotton industry. A carding web as formed by the continuous presentation means 14 therefore contains fibers from a succession of samples 22. Such continuous fiber presentation means are well known in the cotton industry in particular.

The fiber web support 15 is adapted to separate the web from the continuous presentation means 14 and to support the web as it slides over it towards the primary pressing and dispenser means 16 and towards the secondary pressing and dispenser means 17. The means 16 and 17 are in face-to-face relationship and dispense respective continuous films 1 and 46 on either side of the fiber web. The two means 16 and 17 also press the films and the web between the films. The pressing and dispenser means 16 and 17 can dispense aluminum, plastics material or paper film, for example, and vertical forces are applied to their spindles. The pressing and dispenser means 16 and 17 can instead dispense aluminum, plastics material films or paper films and be followed by known type presser rollers.

The heating means 18 and 19 are adapted to evaporate at least some of the water in the fibers and in the defects of the web. The heating means can operate by conduction, for example comprising heated rollers which roll on the film, by forced convection, for example by blowing hot air onto at least one film, and/or by radiation, for example comprising at least one flat heated plate disposed near the films.

Note that the heating means can operate in an asymmetric manner, the film 1 being heated less than the film dispensed by the pressing and dispenser means 17 in order to cause condensation to take place on the film 1.

The cooling means 20 and 21 are adapted to cool both films and the fibers between them. Means of this kind are known.

The upper film separator means 23 are adapted to separate the upper film 46 from the film 1 and are in the form of a spooler, for example.

The material separating means 24 are adapted to separate the film 1 to which are attached the defects 2 without fibers and the defects 3 with their attached fibers 4 from the carding web formed from the sample 22.

Separator means 24 of this kind may comprise, for example, a cylindrical brush rotating clockwise as seen in FIG. 4 and a fiber recovery device (not shown). The separator means 24 may instead comprise a suction device.

The film spooler 25 is adapted to spool the film 1 after it crosses the field of view of the opto-electronic sensor 6.

The opto-electronic sensor 6 is adapted to output an electrical signal representative of images of the film 1, of the defects 2 and 3 and of the fibers 4 between the material separator means 24 and the film spooler 25.

The light source 5 is adapted to illuminate the field of view of the opto-electronic sensor 6. The polarizers 9 and 10 are crossed. Because of this, the output signal of the opto-electronic sensor 6 has different amplitudes for the film 1 and for the defects 2 and 3 and the fibers 4.

The signals representative of images output by the opto-electronic sensor 6 enter the image processing electronic circuit board 26 at its input 30 from which they are routed to the synchronization analyzer 28 and to the threshold comparator 32.

The synchronization analyzer is of a known type. It supplies to the counter 27 a signal indicating a change of line and corresponding to the end, in the signal output by the opto-electronic sensor 6, of the information concerning a line of its optical fields, and a signal indicating changes of points on the line. The counter 27 is adapted to count the change of point signals and is reset by the change of line signal. It supplies to the memories 39 and 40 the number of the point on the line currently output by the opto-electronic sensor 6. The threshold comparator 32 is adapted to output a signal at logic "1" for signals representative of images corresponding to defects 2 and 3 and fibers 4 or a signal at logic "0" for signals representative of images corresponding to the film 1.

The memory 29 is adapted to hold information from the opto-electronic sensor 6 corresponding to a complete line in its optical field, to receive information output by the threshold comparator 32 and to forward the information that it has held to the comparator 31.

The comparator 31 compares the logic values output by the threshold comparator 32 and the memory 29. The logic signal output by the comparator 31 is at "1" if it receives two signals both at logic "1", and at "0" in all other cases. The comparator 31 can be an "AND" gate, for example. Accordingly, it constitutes means of detecting continuity of defects between two line signals successively output by the opto-electronic sensor.

The buffer gate 35 is adapted to hold the highest logical value output by the comparator 31 between two resets. It can therefore comprise a flip-flop, for example.

The rising edge detector 33 is adapted to output a signal at logic "1" when the output of the threshold comparator 32 changes from logic "0" to logic "1".

The output of the rising edge detector 33 is connected to the reset input of the buffer gate 35 and to the write command input of the memory 39.

The falling edge detector 34 is adapted to output a signal at logic "1" when the output of the threshold comparator 32 changes from logic "1" to logic "0".

The output of the falling edge detector 34 is connected to the write command inputs of the memories 36 and 40.

Using this circuit, for each defect 2 or 3 and for each fiber 4 appearing on a line on the film 1 inspected by the opto-electronic sensor 6, the memory 36 holds information on continuity of defects between the two consecutive line signals previously output by the opto-electronic sensor 6, the memory 40 holds the last number of a point on the line corresponding to this defect or fiber and the memory 39 holds the first number of a point on the line corresponding to this defect or fiber.

The memories 36, 39 and 40 can be "First In, First Out" (FIFO) memories. The memory 39 is adapted to output a partial or total filling signal to the transfer signal output 37.

When it receives this signal the computer 44 reads the memories 36, 39 and 40 via the multiplexer 41 using known procedures and devices.

The information received by the computer 44 at its defect information input 42 is simple to process.

To count the total number of defects appearing during a given period, for example the period of 20 seconds laid down by the HVI standard for measuring parameters of cotton, the processing means 1 adds the value "1" to a value in memory for each logic "0" value from the memory 36.

To separate the defects 2 from the defects 3 and the fibers 4 the computer 44 selects the defects and the fibers attached to them in accordance with at least one of their dimensions, for example their length. To this end it includes a threshold comparator for at least one dimension of the defects. Accordingly, defects or spots of sugar 2 with no fibers adhering to them and therefore having a very short length are separated from defects or sticky sugar spots 3 with fibers 4 adhering to them which have a greater length.

Note that the embodiment of the optical part of the device of the invention shown in FIG. 4 can be replaced with any of the embodiments shown in FIGS. 1 to 3 and 5.

Note that the threshold comparator 32 can have a plurality of thresholds adapted to detecting a plurality of different types of defect.

Note that an electronic circuit board such as the image processing electronic circuit board 26 shown in FIG. 4 is not essential to operation of the device, digitization in a computer memory and image processing software being able to implement the same functions or other functions yielding identical results. The image processing electronic circuit board 26 is shown as just one example of fast image processing means that can be used in the device of the invention.

In one variant of the image processing means 7 the image processing electronic circuit board 26 or the computer 44 includes means for measuring the number of photosensitive points on the same line of the opto-electronic sensor perceiving light rays from the same defect.

In a first variant of the device shown in FIG. 4 the film 1 is adapted to absorb at least partly certain liquids and the defects have, at one location at least between the pressing means and the separator means, a liquid phase which can be produced by heating the film 1 using the heating means 18 and 19.

In a second variant of the device shown in FIG. 4 the heating means are incorporated into the pressing means, the films 1 and 46 being heated before they are pressed on to the fiber web produced from the fibrous sample 22.

Figure 5:
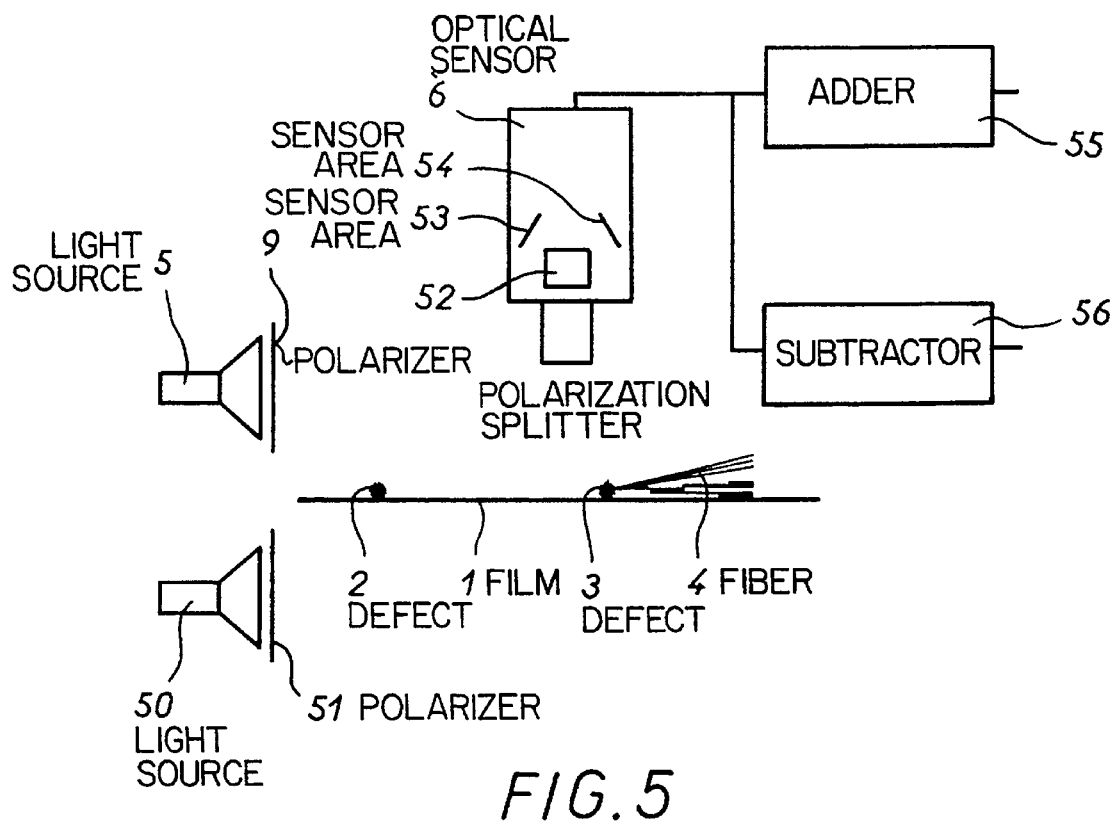
FIG. 5 shows a fourth embodiment of an optical part of the device of the invention.

FIG. 5 shows the film 1, the defects 2 without fibers adhering to them, the defects 3 with fibers 4 adhering to them, two light sources 5 and 50 on respective opposite sides of the film 1 and carrying two respective polarizers 9 and 51, an optical sensor 6 including a polarization splitter 52, two sensor areas 53 and 54, a signal adder 55 and a signal subtractor 56.

In this implementation the film 1 is a partially transmissive material such as paper, blotting paper or cloth, for example.

The polarizers 9 and 51 are crossed. The light sources 5 and 50 are adapted to illuminate both sides of the film 1 equally and uniformly.

The two light sources 5 and 50 are disposed on respective opposite sides of the film and, for points on the film 1 where there is no defect, transmit substantially equal amounts of light towards the opto-electronic sensor.

The polarization splitter 52 is of a known type and is adapted to split the light rays according to their polarization, in order to direct to the sensor area 53 the light rays polarized parallel to the polarization axis of the polarizer 9 and to direct to the sensor area 54 the light rays polarized parallel to the polarization axis of the polarizer 51.

The two sensor areas 53 and 54 can comprise two electronic image sensors, for example. They capture images in a synchronized manner and output synchronized signals, point by point, so that the image information output by the two sensor areas and corresponding to the same point on the film 1 leave the two sensor areas simultaneously.

Accordingly, the opto-electronic sensor 6 is adapted to output a signal representative of at least two images, one of these images representing the optical appearance of the film along one light polarization axis and another of these images representing the optical appearance of the film along a second polarization axis.

The signal adder 55 is adapted to add the signals output by the two sensor areas 53 and 54.

The subtractor 56 is adapted to subtract the two signals output by the two sensor areas 53 and 54.

Depending on the type of defect looked for, the image processing means 7 are connected either to the output of the signal adder 55 or to the output of the signal subtractor 56.

Note that in one variant of the embodiment of the invention shown in FIG. 5 the polarizers 9 and 51 are dispensed with and the opto-electronic sensor 6 is as shown in FIG. 1.

What is claimed as New and Desired to be Secured by Letters Patent of the United States is:

1. Device for detecting defects from fibrous material comprising:

a transfer film;

means for pressing the fibrous material onto the transfer film and transferring defects onto the film;

separating means for separating the fibrous material from the transfer film, the transfer film carrying the defects and fibers adhering to defects, an opto-electronic sensor producing a signal representative of defects on the transfer film in an optical field of the sensor, image processing means connected to the sensor for analyzing the signal issued by the sensor and for counting the defects which are represented by the signal issued by the sensor.

2. Device according to claim 1 for detecting defects which are dispersive for at least one wavelength of polarized light, wherein the film is made from a material which is not dispersive for said wavelength of polarized light, a light source is fitted with a first polarizer to filter a light emitted by the light source on the transfer film in the field of the sensor and a second polarizer disposed on the opto-electronic sensor and oriented to block said non-dispersed polarized light.

3. Device according to claim 1, wherein a heating means heats the film and the fibrous material and causes the defects to adhere to the transfer film, said heating means being disposed between the means for pressing the fibrous material onto the transfer film and the separating means.

4. Device according to claim 1, wherein the opto-electronic sensor outputs a succession of signals representative of transverse lines of the transfer film including a predetermined number of points, the image processing means including means for detecting continuity of a defect between signals representative of successive lines.

5. Device according to claim 4, wherein the image processing means includes means for counting a number of points on a line affected by a same defect.

6. Device according to claim 4, wherein a threshold comparator selects the defects according to at least one of their dimensions.

7. Device according to claim 1, wherein two light sources are disposed on opposite sides of the transfer film, a light that they emit being transmitted by the film in the field of the opto-electronic sensor in substantially equal amounts in the absence of defects.

8. Device according to claim 7, wherein the two light sources are provided with respective polarizers disposed with their polarization axes in quadrature, the opto-electronic sensor being provided with a polarized light splitter and two photo-sensitive areas, the splitter transmitting to each of the two photo-sensitive areas a light polarized parallel to one axis of a polarizer.

9. Device according to claim 1, wherein the transfer film partially absorbs the light at one wavelength at least and the opto-electronic sensor is selectively sensitive at said wavelength.

10. Device for detecting defects from fibrous material comprising:

a transfer film;

means for pressing the fibrous material onto the transfer film and transferring defects onto the film;

separating means for separating the fibrous material from the transfer film, the transfer film carrying the defects and fibers adhering to defects, a light source fitted with a first polarizer to polarize a light emitted by the light source on the transfer film, an opto-electronic sensor producing a signal representative of defects on the transfer film in an optical field of the sensor, a second polarizer is disposed on the opto-electronic sensor and oriented to block said polarized light, image processing means connected to the sensor for analyzing the signal issued by the sensor and for counting the defects which are represented by the signal issued by the sensor.

* * * * *